United States Patent [19]

Yamauchi et al.

[11] Patent Number: 4,965,454

[45] Date of Patent: Oct. 23, 1990

[54] METHOD AND APPARATUS FOR DETECTING FOREIGN PARTICLE

[75] Inventors: Toshihiko Yamauchi; Nobuyuki Akiyama, both of Yokohama, Japan

[73] Assignee: Hitachi, Ltd., Tokyo, Japan

[21] Appl. No.: 298,574

[22] Filed: Jan. 18, 1989

[30] Foreign Application Priority Data

Jan. 21, 1988 [JP] Japan ........................ 63-9482
Feb. 5, 1988 [JP] Japan ........................ 63-23672

[51] Int. Cl.$^5$ .................... G01N 21/47; G01N 21/17; G01N 21/21
[52] U.S. Cl. .................... 250/372; 250/458.1; 250/228; 356/237
[58] Field of Search ............ 250/372, 358.1, 228, 250/458.1, 459.1, 461.1; 356/237, 338

[56] References Cited

U.S. PATENT DOCUMENTS

| | | | |
|---|---|---|---|
| 4,601,576 | 7/1986 | Galbraith | 356/237 |
| 4,602,160 | 7/1986 | Mactaggart | 250/341 |
| 4,626,101 | 12/1986 | Ogawa et al. | 356/237 |
| 4,661,706 | 4/1987 | Messerschmidt et al. | 250/372 |
| 4,669,875 | 6/1987 | Shiba et al. | 356/237 |
| 4,740,708 | 4/1988 | Batchelder | 356/237 |
| 4,873,430 | 10/1989 | Juliana et al. | 250/225 |
| 4,902,131 | 2/1990 | Yamazaki et al. | 356/336 |

*Primary Examiner*—Constantine Hannaher
*Assistant Examiner*—Edward J. Glick
*Attorney, Agent, or Firm*—Fay, Sharpe, Beall, Fagan, Minnich & McKee

[57] ABSTRACT

The present invention resides in a method and apparatus for detecting a foreign particle, wherein an ultraviolet light beam is radiated in the form of a spot to a sample having a protective film formed on a circuit pattern or a wiring pattern; the spot and the sample are scanned relative to each other; the ultraviolet light is absorbed by the protective film; diffracted light produced from a foreign particle present on the protective film is condensed by an integrating sphere; the thus-condensed light is sensed by an optoelectro transducer to convert it into an electric signal; and the foreign particle present on the protective film formed on the circuit pattern or the wiring pattern is detected on the basis of the electric signal provided from the optoelectro transducer.

13 Claims, 7 Drawing Sheets

AN INCIDENT ANGLE OF P-
POLARIZATION OF LIGHT (i1)

METHOD AND APPARATUS FOR DETECTING FOREIGN PARTICLE

BACKGROUND OF THE INVENTION

The present invention relates to a method and apparatus for detecting, in high sensitivity, a foreign particle present on an organic protective film having an underlying circuit pattern or wiring pattern such as an X-ray exposure mask or a semiconductor wafer.

Known conventional foreign particle detecting apparatus are, for example, the apparatus described in Japanese Patent Laid-Open No. 186324/84 and an apparatus wherein the upper surface of a wafer is scanned spotwise using a laser light of 488 nm or 780 nm in wavelength, then scattered light due to the presence of a foreign particle is condensed by an integrating sphere and the thus condensed light is sensed by an optoelectro transducer to detect the foreign particle.

In such conventional foreign particle detecting apparatus, however, no consideration is given to the technical subject of detecting a foreign particle present on the organic protective film having an underlying circuit pattern or wiring pattern, in high sensitivity without being influenced by the light reflected from the circuit pattern or wiring pattern.

Though not directly related to the present invention, reference is here made to the following literature as literature showing a related art, wherein a transparent thin film called pelicle is provided on a mask to prevent a foreign particle from directly adhering onto the mask: Koizumi et al. "Hand Book for Automated System in Modern Semiconductor Factory" separate volume, Science Forum (July 25, 1984), p. 342.

However, in the case of a mask for X-ray exposure, it is necessary that the spacing between the mask and a substrate not be larger than 30 μm, thus making it impossible to form pelicle on the mask, and so it is required to strictly check metallic foreign particles which do not transmit X-ray.

SUMMARY OF THE INVENTION

The present invention has been accomplished to solve the above-mentioned problem and it is a primary object thereof to provide a method and apparatus capable of detecting a foreign particle present on an organic protective film having an underlying circuit pattern or wiring pattern, in high sensitivity without being influenced by the light reflected from the circuit pattern or wiring pattern.

It is another object of the present invention to provide a method and apparatus also capable of eliminating the influence of unevenness of the surface of the above organic protective film caused by the unevenness of the above circuit pattern or wiring pattern, thereby permitting detection of a foreign particle.

It is a further object of the present invention to provide a method and apparatus capable of detecting a metallic fine foreign particle which markedly attenuates X-rays with respect to the surface and the back of an X-ray exposure mask.

According to the present invention, in order to achieve the aforementioned primary object, an ultraviolet light beam is radiated spotwise to a sample which has an organic protective film on a circuit pattern or a wiring pattern, to scan the sample in a relative manner; then diffracted light from a foreign particle present on the organic protective film is condensed by an integrating sphere. The thus condensed light is sensed and converted to an electric signal by means of an optoelectro transducer; and the foreign particle is detected on the basis of the signal. Thus, the ultraviolet light beam radiated is absorbed by the organic protective film to eliminate the reflection from the circuit pattern or the wiring pattern, allowing diffracted light from the foreign particle to be condensed efficiently (effectively) by the integrating sphere, thus permitting detection of foreign particles The present invention further resides in detecting a foreign particle by means of an integrating detection system wherein, when there is unevenness on the surface of the organic protective film, a light shielding plate is inserted in the integrating sphere such that the shielding plate functions to separate low-order diffracted light produced by surface undulation and inducing the detection of scattered light from the foreign particle.

According to one construction of the present invention, in a method for detecting a foreign particle present on an X-ray exposure mask which is for exposing a semiconductor, etc. through a pattern using X-ray, an organic film having a minimum thickness at which the film absorbs most of the light in a specific ultraviolet light region other than the wavelength region of the X-ray used for the exposure of the pattern, is formed on the same pattern; P-polarization of light having a wavelength in the specific region is directed to the organic film at Brewster's angle as an incident angle; and whether scattered light is present or not is detected to detect a foreign particle. According to another construction of the invention, a substrate for the pattern of the X-ray exposure mask has as a main constituent a first organic film having a minimum thickness at which the film absorbs most of the light in a specific ultraviolet light region other than the wavelength region of the X-ray used for the exposure of the pattern; a second organic film similar to the first organic film is formed on the pattern; and a light having a wavelength in the specific region is radiated at a vertical incident angle to the substrate side, while P-polarization of light having a wavelength in the specific region is radiated to the pattern side at Brewster's angle as an incident angle, then whether scattered light is present or not is detected to detect a foreign particle.

Thus, in the present invention, an organic film is formed on the circuit pattern or wiring pattern and an ultraviolet light beam (wavelength: not larger than 380 nm) is applied to the organic film and scattered light from the surface of the same film is detected. The radiated light is absorbed by the organic film, not reaching the circuit pattern or the wiring pattern. Therefore, there will be no scattered light from such a pattern.

On the other hand, if there is a foreign particle on the organic film, the radiated light will be scattered strongly by the foreign particle, so by detecting the scattered light (diffracted light) from the surface of the organic film continually it is possible to detect the foreign particle.

However, if the organic film surface has unevenness, there will be detected specularly reflected light induced by the unevenness together with scattered light from the foreign particle. In this case, it is impossible to make a distinction between the foreign particle and the unevenness, thus causing an erroneous detection. To avoid this inconvenience, the detection is made either in Brewster's angle or by using an integrating sphere with a light shielding plate inserted therein. The shielding plate functions to shield specularly reflected light and low-order diffracted light from the unevenness which induces the detection, whereby it becomes possible to detect only the scattered light from a foreign particle.

DETAILED DESCRIPTION OF THE PREFERRED EMBODIMENTS

Embodiments of the present invention will be described herein with reference to the accompanying drawings.

Figure 1:
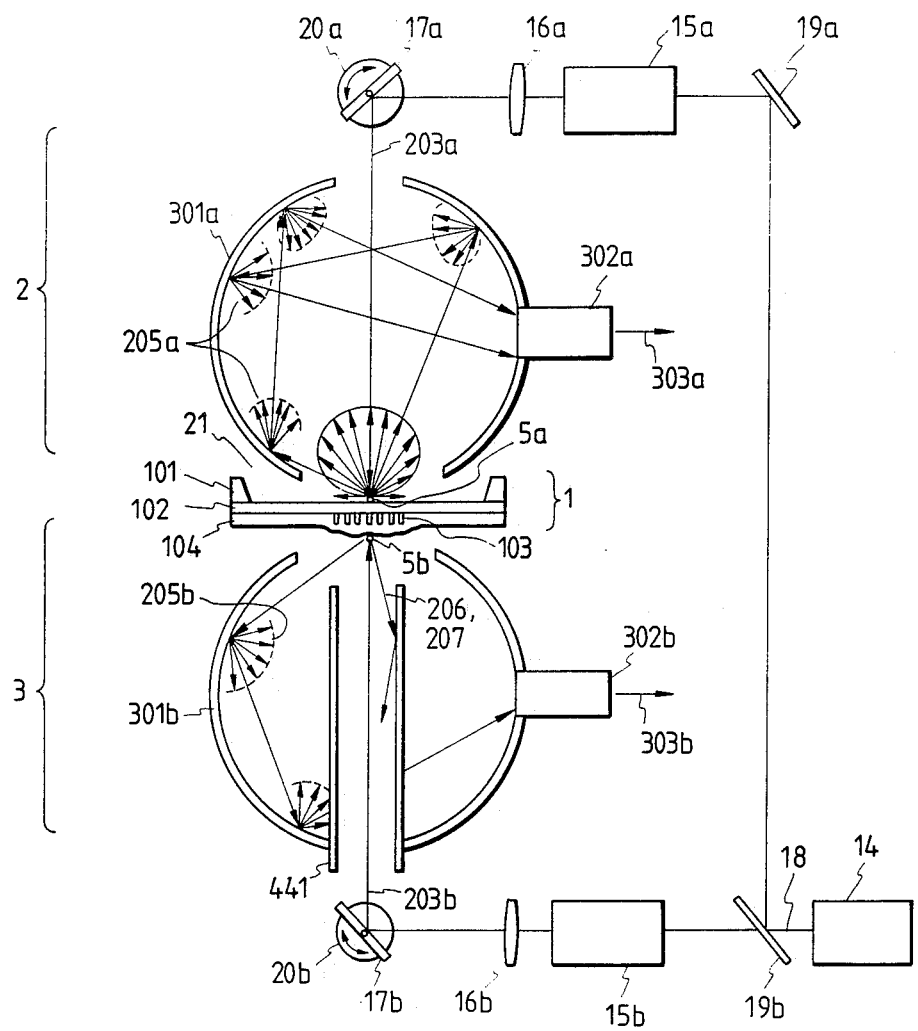
FIG. 1 is a sectional view showing basic constructions of two embodiments according to the present invention.

Referring first to FIG. 1, there are shown a construction of an X-ray mask having an organic protective film formed thereon and that of illumination and integrating sphere detection systems. As shown in the same figure, the X-ray mask 1 is composed of a support member 101 formed in the shape of a frame using a material such as silicon, a substrate 102 formed using a material such as boron nitride (BN) or silicon nitride ($Si_3N_4$), a circuit pattern 103 formed using a material such as gold (Au), and an organic protective film (e.g. polyamide film: polyamide iso-indroquinazolinedione) 104.

On the support member 101 side there is no surface unevenness of the substrate 102 because the substrate is sufficiently thick. On the substrate side, therefore, light 205a scattered from a foreign particle is condensed by a scattered light detection system 2 constituted by only an integrating sphere 301a (light is scattered by the inner surface of the sphere and becomes reflected light), then sensed by an optoelectro transducer 302a, which outputs a detection signal 303a to detect the foreign particle.

The organic film 104 is formed on the circuit pattern 103. The numeral 12 shown in FIG. 4 denotes a stage having a holder portion 11 for holding the X-ray mask 1. Numerals 203a and 203b each denote a what are generally called a detecting light beam and is more specifically disclosed as an ultraviolet light beam for detecting the foreign particle 5a. The detecting light beam being radiated from a laser light source 14 with a wavelength not larger than 380 nm. Numerals 15a and 15b each denote a beam expander; numerals 16a and 16b each denote a light condensing lens; numerals 17a and 17b each denote a galvanomirror (rotating mirror), the mirrors 17a and 17b being swung by motors 20a and 20b, respectively; numerals 2 and 3 each denote a scattered light detecting system.

Figure 4:
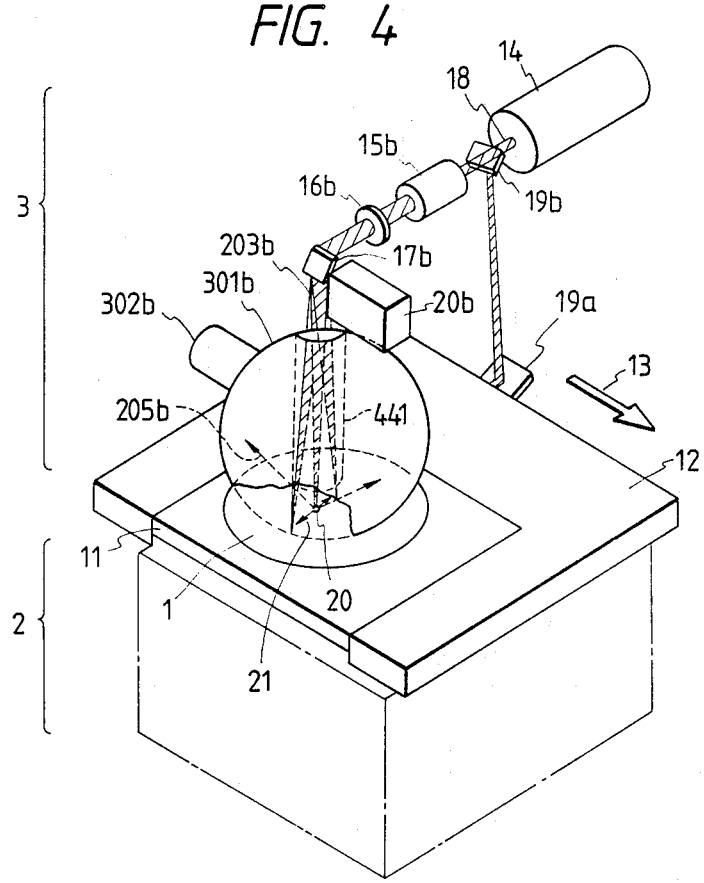
FIG. 4 is a perspective view showing one of the two embodiments of the apparatus constructed on the basis of the principle illustrated in FIG. 1.

Further, the numeral 20 shown in FIG. 4 denotes a focused spot; numeral 13 also shown therein represents a moving direction of the stage 12; numeral 21 represents a light scanning direction; numerals 205a and 205b each represent scattered light from the foreign particle 5a, 5b. Numerals 19a and 19b denote half mirrors for branching a laser light beam 18 not larger than 380 nm in wavelength.

Figure 3:
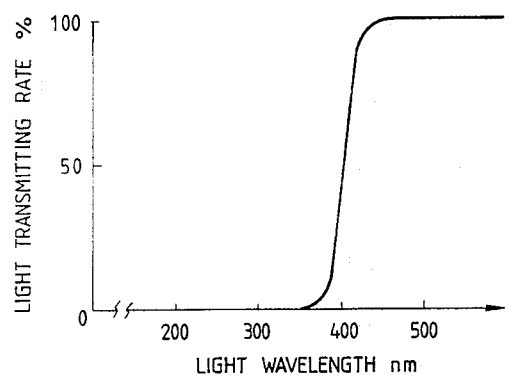
FIG. 3 is a cartesion coordinate system showing a spectral light transmitting rate of the organic protective film of the X-ray mask of FIG. 2.

The organic protective film 104 uses a polyamide film. As to a spectral light transmitting rate of the polyamide film, this film has the property that its light transmitting rate for light not larger than 380 nm in wavelength is extremely small, as is seen from FIG. 3 wherein wavelength (nm) and light transmitting rate are plotted along the axis of abscissa and the axis of ordinate, respectively. On the other hand, for shorter wavelengths (1–20 nm) such as X-rays, the polyamide film exhibits a value of light transmitting rate near 100%. Therefore, even if the organic protective film 104 is formed on the circuit pattern 103 formed of gold for example, it is possible to positively effect the transfer of the same pattern.

Figure 2:
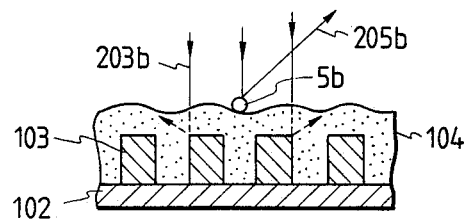
FIG. 2 illustrates an X-ray mask with laser light applied to an organic protective film side.

If the polyamide film is formed as the organic film 104 on the X-ray mask, as shown in FIG. 2, the foreign particle 5b in the air will adhere onto the film. In the inspection of a foreign particle, when the detecting light 203b having a wavelength not larger than 380 nm is radiated from above, the light portion impinged on the polyamide film is absorbed by the polyamide film, so scattered light is not produced, while the light portion which has impinged on the foreign particle 5b produces scattered light (diffracted light) 205b, so the detection of the foreign particle can be effected by merely detecting the scattered light 205b by the scattered light detecting system 3.

As shown in FIG. 4, the mask 1 having organic film 104 formed thereon is set on the stage 12 which is movable uniaxially, and is moved in the direction of arrow 13.

On the other hand, the laser light beam 18 from the laser source 14, having a wavelength not larger than 380 nm, is expanded in diameter by the beam expanders 15a and 15b and then condensed as a laser light spot by the light condensing lenses 16a and 16b. And the laser light spot is drifted in the scanning direction 21 by the galvanomirrors 17a and 17b. By so doing, the laser light spot scans the whole surface of the circuit pattern on the substrate side and the organic protective film side, so that the scattered lights 205a and 205b are condensed by the scattered light detecting systems 2 and 3 and detected by the optoelectro transducers 302a and 302b, whereby the foreign particle 5a, 5b can be detected.

The thickness of the organic protective film 104 of the X-ray exposure mask will now be explained. If the light reflected and scattered from the circuit pattern 103 of the mask in the presence of the organic protective film is $I_1$ and that in the absence of the organic protective film is $I_2$ and the incident light is $I_0$, it is necessary in the present invention to set the thickness of the organic protective film so that the pattern scattered light ratio $k_2 = I_2/I_0$ in the presence of the organic protective film is not greater than about 0.1% of the pattern scattered light ratio $k_1 = I_1/I_0$ in the absence of the organic protective film. That is, it is necessary for the organic protective film to have a thickness not larger than about 0.001 in terms of $K_2/k_1$.

On the other hand, since there is a relation of $T = 10^{-3.0 \times l}$ between the light transmitting rate, T, of the organic protective film at a wavelength of 325 nm and the thickness, 1 μm, of the organic protective film, it is necessary for the same film to have a thickness of 1 μm in order that the scattered light ratio $k_2 = I_2/I_0$ in the presence of the film may become about 0.1% of the circuit pattern scattered light ratio $k_1 = I_1/I_0$. However, since the incident light reciprocates through the organic protective film between the film and the circuit pattern, the film thickness required may be 0.5 μm.

Therefore, in order to obtain a $k_2/k_1$ ratio not larger than 0.001, it is necessary for the organic protective film to have a thickness of at least 0.5 μm. This film thickness is necessary for protecting the circuit pattern 103. Thus, it is possible to eliminate the influence of the reflected light from the circuit pattern 103 almost completely.

Figure 5:
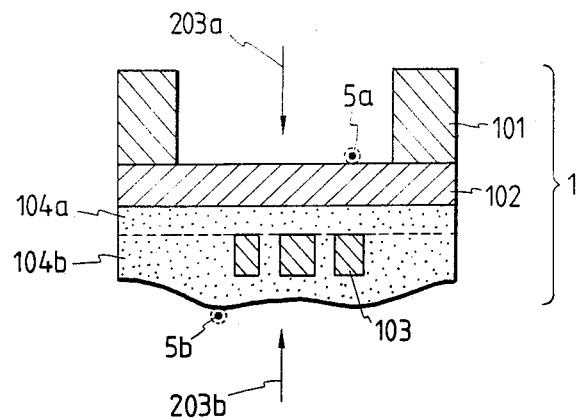
FIG. 5 is an explanatory view of another X-ray exposure mask.

FIG. 5 is an explanatory view of an X-ray exposure mask. This mask, indicated at 1, comprises a substrate 102 formed of a material such as, for example, boron nitride (BN) or silicon nitride ($Si_3N_4$) and a frame 101 formed of a material such as, for example, silicon (Si). On the substrate 102 is formed in a thickness of about 3 pm an organic protective film 104a which transmits X-rays, and on the film 104a is formed a circuit pattern 103 using gold (Au) having a thickness of about 1 μm. Further, an organic protective film 104b which transmits X-rays is formed on the circuit pattern 103 in a thickness of about 5 μm.

The X-ray exposure mask constructed as above is irradiated with ultraviolet light beams 203a and 203b of not larger than 380 nm in wavelength from both the substrate 102 side and the side opposite thereto to detect the foreign particles 5a, 5b on the mask 1 in the same manner as described previously.

Although in the above embodiments there were employed X-ray exposure masks having light-absorbing organic protective film(s), there is no limitation in the invention to such X-ray exposure masks provided any substitute fulfills the same function. It is apparent that the same function will be attained also in the case of a semiconductor device (e.g. wafer or a multi-layered thin film substrate) having a circuit pattern and also having an organic protective film such as a resist film formed thereon.

Thus, without being influenced by the circuit pattern, it is possible to effect the detection of a foreign particle not larger than 0.15 μm which has heretofore been impossible. For example, in the case of an X-ray exposure mask, once a foreign particle is detected, it is possible to remove it by washing or any other suitable means, with the result that exposure can be effected in a foreign particle-free condition, thus greatly contributing to the yield of LSI.

Figure 6:
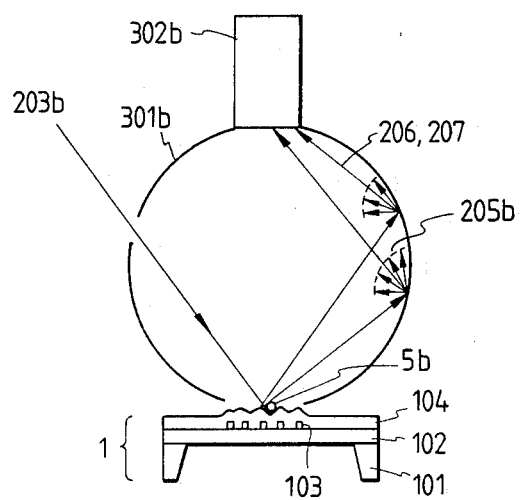
FIG. 6 is an explanatory view for explaining light characteristics due to uneven surfaces.

On the circuit pattern side, since the organic protective film 104 is thin, there occurs unevenness on the film surface due to stepped portions of the circuit pattern 103. As shown in FIG. 6, all scattered light 205b from a foreign particle 5b as well as specularly reflected light 206 and diffracted light 207 from the surface unevenness enter an integrating sphere 301b (the inner surface scatters and reflects light) and reach a detector 302b, so it is impossible to distinguish between the unevenness and the foreign particle in a signal.

The following is an explanation about a Brewster's angle illumination and detection method.

Figure 7:
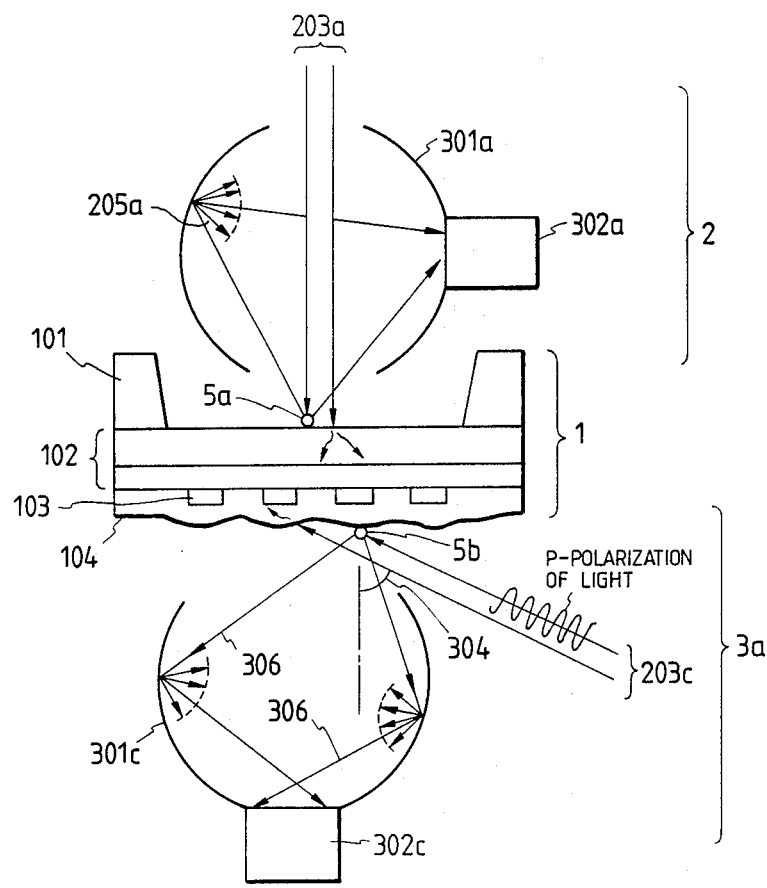
FIG. 7 is a sectional view showing basic construction of another embodiment of the invention.

FIG. 7 shows a construction of an X-ray mask 1 having an organic protective film 104 and that of an illuminating and detecting method. As shown in the same figure, the X-ray mask 1 is composed of a support member 101, a substrate 102, a circuit pattern 103 and an organic protective film 104.

On the support member 101 side there is no surface unevenness of the substrate 102 because the substrate is sufficiently thick. On the substrate side, therefore, the detection of a foreign particle can be made using a coaxial downward illumination portion in the detection system 2.

On the other hand, on the organic protective film side, included in another detection system 3a, there occurs surface unevenness of the organic protective film due to stepped portions of the circuit pattern because the film is thin. However, by performing illumination and detection using P-polarization of light at Brewster's angle according to the present invention in a detection system 3a, it is possible to eliminate specularly reflected light caused by surface unevenness nearly completely. This is based on the following principle.

Figure 8:
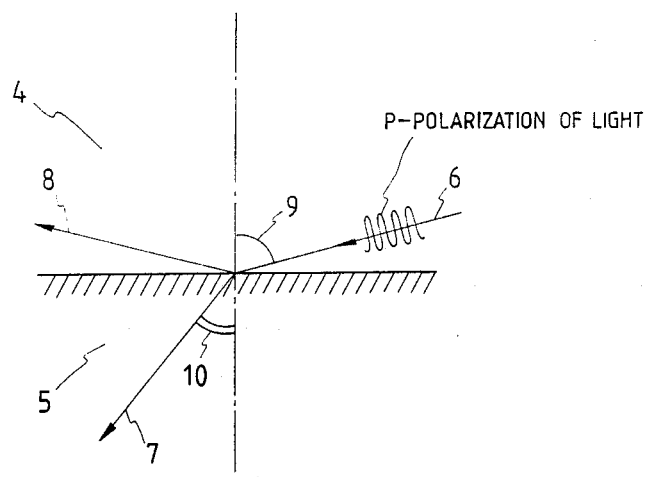
FIG. 8 is a view showing a reflection characteristic obtained when P-polarization of light is radiated at Brewster's angle.
Figure 9:
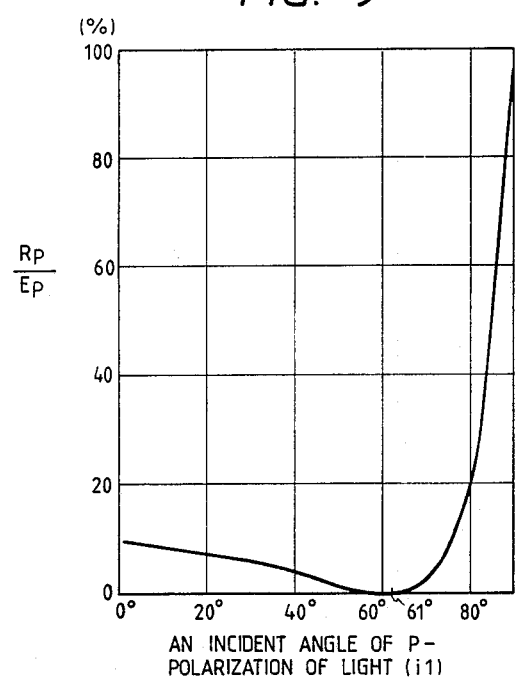
FIG. 9 is a graph showing a relationship between an incident angle, $i_1$, and Rp/Ep.

As shown in FIG. 8, where a linear polarized light is incident on materials different in refractive index, the intensity $R_p$ of a reflected light 8 depends on an incident angle 9 (i1). If the intensity and refraction angle 10 of a P-polarized incident light 6 are $E_p$ and $i_2$, respectively, the refractive index of a medium 4 is n and that of a medium 5 is n', the $R_p/E_p$ ratio may be written as follows using Fresnel's formula:

$$\frac{R_p}{E_p} = \frac{\tan\left(i_1 - \sin^{-1}\left(\frac{n}{n'} \sin i_1\right)\right)}{\tan\left(i_1 - \sin^{-2}\left(\frac{n}{n'} \sin i_1\right)\right)} \quad (1)$$

where n<n'. The details are described in "Applied Optics" pp. 146-149.

Where illumination is made using P-polarization of light, the refractive index of the organic protective film 109 is n'1.8, so the $R_p E_p$ ratio can be calculated using the above equation (1) and the result is as illustrated in FIG. 9. From this figure it is seen that the ratio is zero at $i_1 = 61°$ and can be kept below 0.5% in the range of $61° \pm 5°$.

Therefore, where the refractive index n'=1.8 is used, if the illumination angle of P-polarization of light is set at 61°, it is possible to detect scattered light from a foreign particle without being influenced by light from the unevenness of the organic protective film 104. As to the illumination using S-polarization of light, it is not appropriate because there is no very small angle of $R_p/E_p$.

Figure 10:
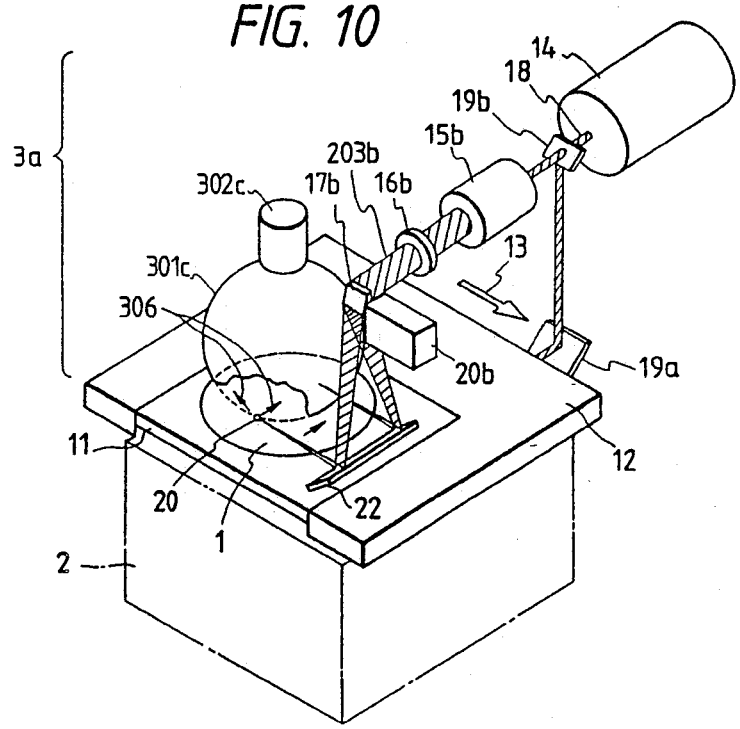
FIG. 10 is a perspective view showing an apparatus which has been constructed on the basis of the principle illustrated in FIG. 7.

Referring now to FIGS. 7 and 10, there is illustrated further embodiments of the present invention, wherein a mask 1 having an organic protective film thereon is held by a holder portion 11 and scanned in the direction of arrow 13 by means of a uniaxial stage 12 capable of making a double-side inspection. On the other hand, as the illumination light there is used a light beam 18 of a wavelength not larger than 380 nm radiated from a laser source 14. The light 18 is expanded in diameter by a beam expander. 15b and a P-polarized laser light 203c is condensed to a spot 20 at Brewster's angle not larger than 304° through a light condensing lens 16b and a Brewster's angle illumination mirror 22. Between the lens 16b and the mirror 22 is disposed a galvanomirror 17b to drift the spot 20 in a direction perpendicular to the arrow 13. By so doing, the spot 20 scans the whole surface of the mask; therefore, by detecting scattered light 306 in synchronism with the scanning through a light collector 301c and a detector 302c, it is possible to realize an apparatus capable of detecting a foreign particle without being influenced by the surface unevenness of the organic protective film. In short, a foreign particle present on the organic protective film 104 which has unevenness can be detected by the Brewster's angle illumination/detection optical system indicated at 3a.

Figure 11:
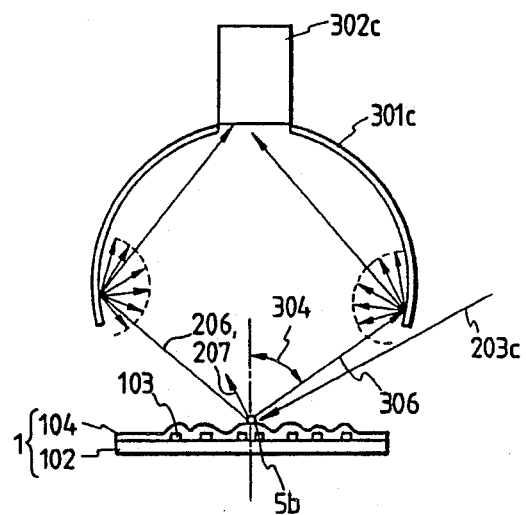
FIG. 11 is a view for explaining the outcome of disordering P-polarization of an illuminating light.

On the other hand, where the Brewster's angle illumination and detection method shown in FIG. 7 is used, if the illumination with P-polarization of light is not extinguished on the surface of the organic protective film, then it is possible for this technique to detect only scattered light from the foreign particle. As shown in FIG. 11, however, if P-polarization of the illumination light 203c is disordered even to a slight extent, there will occur specularly reflected light 206 and diffracted light 207, making it impossible to distinguish between foreign particle and unevenness.

In this connection, as shown in FIGS. 1 and 4, if there is used a detection system 3 using an integrating sphere with a cylindrical light shielding plate 441 inserted therein. The shielding plate separates a specularly reflected light, the specularly reflected light 206 and the diffracted light 207 which causes erroneous detection are shielded by the light shielding plate 441 and therefore do not enter the integrating sphere, thereby permitting scattered light 205b from the foreign particle to be detected emphatically. This is based on the following principle.

Figure 12:
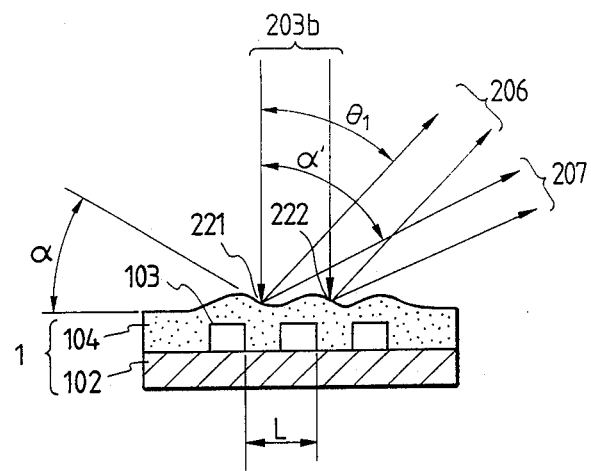
FIG. 12 is a view showing a reflection characteristic obtained by radiating laser light vertically to an organic protective film.

When light is incident on an inclined small surface 221 as shown in FIG. 12, there is produced specularly reflected light at an inclination angle, $\alpha$, of the surface and at the same time diffracted light 207 is produced by interference with the light reflected from an inclined small surface 222 adjacent to the surface 221. In this case, the angle, $\theta_1$, of the specularly reflected light is obtained as $\theta = \alpha 2$. On the other hand, the angle, $\alpha'$, of m-order diffracted light is determined as follows using the spacing between the inclined surfaces 221 and 222, i.e., a pattern spacing L in the organic protective film, and the wavelength, $\lambda$, of the illumination light:

$$\alpha' = \sin^{-1}\left(\frac{m\lambda}{L}\right) \quad (m = 0, \pm 1, \pm 2 \ldots) \quad (2)$$

Further details are described in "Physical Optics," Kyoritsu Shuppan, pp. 101-113.

In this connection, there should be noted a magnitude relation between the intensity, $I_{par}$, of scattered light from the foreign particle and the intensity, $I_{ref}$, of the specularly reflected light as well as the intensity, $I_{def.m}$ of the m-order diffracted light. The following relationship exists between them if the intensity of the incident light is $I_{in}$ and the component absorbed is $I_T$:

$$I_{in} = I_T + I_{ref.} + \sum_{m=-\infty}^{+\infty} I_{def.m} \quad (3)$$

As to $I_{ref}$, since it is double the inclination angle $\alpha$ of unevenness as noted above, it is easy to set a light shielding plate to shield it, and by inserting the light shielding plate into the integrating sphere it is possible to make $I_{ref}$ entering the same sphere zero. On the other hand, as to $I_{def.m}$, it is seen from the equation (2) that the angles of generation take variance values and that most diffracted light energy is concentrated on $\pm 1$ to $\pm 2$ order diffracted light rays (see the foregoing "Physical Optics's"). In consideration of these facts, if all of diffracted light rays below a certain k order are shielded and $I_{ref}$ is set equal to 0 (zero), it is possible to obtain:

$$I_{par.} \geq 3 \cdot \left(\sum_{m=|h|}^{\pm\infty} I_{def.m}\right)$$

The numeral "3" on the right-hand side of the above expression is a guideline for showing that at such a degree of ratio it is possible to determine only $I_{par}$ by performing a binarization processing electrically after the detection.

Figure 13:
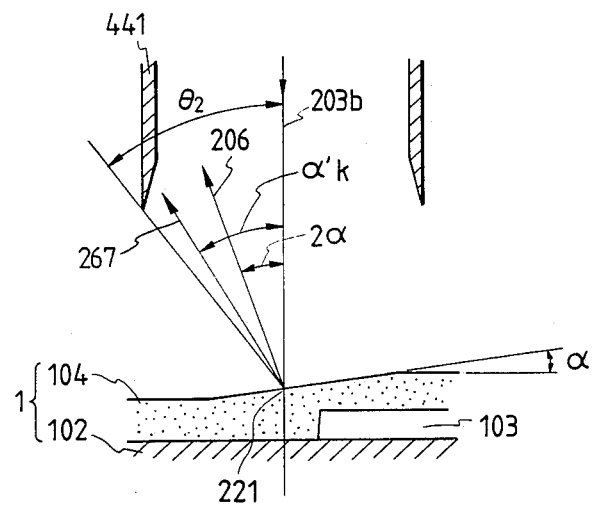
FIG. 13 shows an angle for a light shielding plate to suitably detect a foreign particle.

In the detection, therefore, it is possible to distinguish between the surface unevenness of the organic protective film and a foreign particle by suitably setting a light shielding angle $\theta_2$ of the light shielding plate 441 so as to permit shielding of a generation angle $\alpha'_k$ of k-order diffracted light 267 and the angle, $2\alpha$, of the specularly reflected light, as shown in FIG. 13.

For example, in the X-ray mask presently in use, the maximum value of the inclination of unevenness is $\alpha = 7$ and hence $2\alpha = 14°$, and in $L \leq 4$ μm (it has been made clear experimentally that at $L \leq 4$ μm there is not developed surface unevenness of the organic protective film), if the wavelength of illumination light is $\lambda = 0.325$ μm, the value of m which satisfies the equation (3) is 6. And at this time, $\alpha' = 26°$. Therefore, if the light shielding angle $\theta_2$ of the light shielding plate 441 is set at $\theta \geq 26°$ in the detection, it is possible to detect a foreign particle of 0.15 μm as a target size to be detected, at:

$$I_{par.} (0.15 \mu m) \geq 3 \cdot \left(\sum_{m=6}^{\pm\infty}\right) I_{def.m}$$

In the embodiment of the invention illustrated in FIGS. 1 and 4, the X-ray mask 1 having the organic protective film 104, which has been explained in connection with the detection method using only integrating spheres, is supported by the holder portion 11 and is scanned in the direction of arrow 13 by the uniaxial stage 12 capable of performing a double-side inspection. On the other hand, as the illumination light beam 203b there is used a light beam 18 of not larger than 380 nm in wavelength, which is expanded in diameter by the beam expander 15b and thereafter condensed to a spot 20 through the light condensing lens 16b. Between the lens 16b and the spot 20 is disposed a galvanomirror 17b to shift the spot 20 in directions perpendicular to the arrow 13. As a result, the spot scans the whole surface of the circuit pattern of the mask 1, so scattered light can be detected in synchronism with the scan through the integrating sphere 301b and the optoelectro detector 302b which allows output of a detection signal 303b. Diffracted light rays up to m-order from the surface unevenness are prevented from entering the sphere 301b by cylindrical light shielding plate 441 having a light shielding angle θ.

In this way it is possible to realize an apparatus capable of detecting a foreign particle present on the mask without being influenced by the surface unevenness.

It is desirable for the cylindrical light shielding plate 441 to have an outer surface held in a condition of mirror surface superior in reflectivity.

According to the present invention, as set forth hereinabove, it is possible to detect a foreign particle not larger than 0.15 μm without being influenced by the circuit pattern or the surface unevenness of the organic protective film. Consequently, where the sample is a mask, it is possible to greatly reduce the occurrence of defects of the pattern caused by the transfer of a foreign particle present on the mask during exposure, thus greatly contributing to the improvement in yield of LSI products.

We claim:

1. A method for detecting a foreign particle comprising the steps of:
   radiating an ultraviolet light beam having a wavelength not larger than 380 nm in the form of a spot to a sample comprising at least one of a circuit pattern and a wiring pattern formed on a substrate and an organic protective film formed on the pattern;
   allowing said spot and said sample to scan relatively to each other;
   allowing said ultraviolet light to be absorbed by said organic protective film;
   condensing diffracted light from the foreign particle present on the organic protective film by means of an integrating sphere;
   sensing the condensed light by means of an optoelectro transducer to convert the condensed light into an electric signal; and
   detecting the foreign particle on said organic protective film in accordance with said electric signal.

2. A method for detecting a foreign particle comprising the steps of:
   radiating an ultraviolet light beam in the form of a focused light spot having a wavelength not larger than 380 nm, to an x-ray exposure mask comprising a circuit pattern formed on a substrate and an organic protective film formed on the circuit pattern;
   allowing said focused light beam and the x-ray exposure mask to scan relatively to each other;
   allowing said ultraviolet light beam to be absorbed by said organic protective film of the x-ray exposure mask;
   condensing diffracted light from the foreign particle present on the organic protective film by means of an integrating sphere;
   sensing the condensed light by means of an optoelectro transducer to convert the condensed light into an electric signal; and
   detecting the foreign particle on said organic protective film in accordance with said electric signal.

3. A method for detecting a foreign particle comprising the steps of:
   radiating an ultraviolet light beam to a sample comprising at least one of a circuit pattern and a wiring pattern formed on a substrate, and an organic protective film formed on the pattern;
   allowing said ultraviolet light to be absorbed by said organic protective film,
   separating low-order diffracted light and high-order diffracted light both produced from a foreign particle on a surface of said organic protective film, from each other;
   condensing the high-order diffracted light by means of an integrating sphere;
   sensing the condensed light by means of an optoelectro transducer to convert the condensed light into an electric signal; and
   detecting the foreign particle on the organic protective film in accordance with said electric signal.

4. A method for detecting a foreign particle according to claim 3, wherein said ultraviolet light beam has a wavelength not larger than 380 nm.

5. An apparatus for detecting a foreign particle comprising;
   means for radiating an ultraviolet light beam having a wavelength not larger than 380 nm in the form of a spot to a sample comprising at least one of a circuit pattern and a wiring pattern formed on a substrate and an organic protective film formed on the pattern so as to absorb the ultraviolet light beam into the organic protective film of the sample;
   an integrating sphere for condensing diffracted light produced from the foreign particle present on the protective film of said sample which absorbs the ultraviolet light beam;
   an optoelectro transducer for converting the condensed diffracted light into an electric signal;
   means for scanning said spot of the ultraviolet light beam for radiation, said integrating sphere and said optoelectro transducer in relative relation to said sample; and
   wherein the foreign particle on said organic protective film is detected in accordance with said electric signal obtained from said optoelectro transducer by absorbing the radiation ultraviolet light beam into the organic protective film.

6. An apparatus for detecting a foreign particle comprising:
   means for radiating an ultraviolet light beam to a sample comprising at least one of a circuit pattern and a wiring pattern formed on a substrate and an organic protective film formed on the pattern so as to absorb the ultraviolet light beam into the organic protective film of the sample;
   a light shielding means for separating low-order diffracted light and high-order diffracted light, both produced from a foreign particle on the surface of the organic protective film, from each other;
   a light condensing optical system for condensing high-order diffracted light separated by said light shielding means;

an optoelectro transducer for converting the light condensed by said light condensing optical system into an electric signal; and wherein the foreign particle is detected in accordance with the basis of the electric signal provided from said optoelectro transducer.

7. The apparatus for detecting a foreign particle according to claim 6, wherein said radiating means is constructed so as to radiate the light beam in a direction perpendicular to the sample, and said light shielding member is a cylindrical member having an axis perpendicular to the sample and having an outer surface formed as a mirror surface.

8. The apparatus for detecting a foreign particle according to claim 6, wherein said light condensing optical system, comprises an integrating sphere.

9. A method for detecting a foreign particle present on an x-ray exposure mask for the exposure of a semiconductor or the like to a pattern using an x-ray beam, wherein said pattern of said x-ray exposure mask is formed on an organic film having a minimum thickness at which the film absorbs most of a specific wavelength region of light other than the wavelength region of the x-ray beam used for the pattern exposure, and that P-polarization of light having a wavelength in said specific wavelength region is radiated to said organic film at Brewster's angle as an incident angle such that whether scattered light is present is detected in order to detect the foreign particle.

10. The method for detecting a foreign particle according to claim 9, wherein said specific wavelength region of light has a wavelength not larger than 380 nm.

11. A method for detecting a foreign particle present on an x-ray exposure mask for the exposure of a semiconductor or the like to a pattern using an x-ray beam, wherein a substrate for the pattern of said x-ray exposure mask has as a main constituent a first organic film having a minimum thickness at which the film absorbs most of a specific wavelength region of light other than the wavelength region of the x-ray used for the pattern exposure, that a second organic film similar to the first organic film is formed on said pattern, that said specific wavelength region of light is radiated to the substrate side at a vertical incident angle, while P-polarization of light having a wavelength in said specific wavelength region is radiated to the pattern side at Brewster's angle as an incident angle, and that whether scattered light is present is detected in order to detect the foreign particle.

12. The method for detecting the foreign particle according to claim 11, wherein said specific wavelength region of light has a wavelength not larger than 380 nm.

13. The method for detecting a foreign particle according to claim 3, wherein the ultraviolet light beam is formed by the P-polarization light beam, said ultraviolet light beam being radiated to the protective film of the sample at Brewster's angle as an incident angle.

* * * * *

UNITED STATES PATENT AND TRADEMARK OFFICE
CERTIFICATE OF CORRECTION

PATENT NO. : 4,965,454

DATED : October 23, 1990

INVENTOR(S) : Yoshihiko Yamauchi and Nobuyuki Akiyama

It is certified that error appears in the above-identified patent and that said Letters Patent is hereby corrected as shown below:

ON TITLE PAGE:

The names of the inventors should appear on the patent as follows:

Yoshihiko Yamauchi and Nobuyuki Akiyama (Mr. Yamauchi's first name is misspelled on the original Letters Patent).

Claim 5, column 10, line 51, please delete "radiation" and insert therefor --radiating--.

Signed and Sealed this

Twenty-fifth Day of February, 1992

*Attest:*

HARRY F. MANBECK, JR.

*Attesting Officer*     *Commissioner of Patents and Trademarks*